(12) United States Patent
Shoham et al.

(10) Patent No.: US 10,386,311 B1
(45) Date of Patent: *Aug. 20, 2019

(54) SYSTEM AND METHOD FOR DEFECT DETECTION USING MULTI-SPOT SCANNING

(71) Applicant: Applied Materials Israel, Ltd., Rehovot (IL)

(72) Inventors: Amir Shoham, Nes-Ziyyona (IL); Yoav Berlatzky, Beit Guvrin (IL); Haim Feldman, Nof-Ayalon (IL)

(73) Assignee: APPLIED MATERIALS ISRAEL, LTD., Rehovot (IL)

(*) Notice: Subject to any disclaimer, the term of this patent is extended or adjusted under 35 U.S.C. 154(b) by 0 days.

This patent is subject to a terminal disclaimer.

(21) Appl. No.: 15/803,789

(22) Filed: Nov. 5, 2017

Related U.S. Application Data

(62) Division of application No. 14/037,304, filed on Sep. 25, 2013, now Pat. No. 9,810,643.

(60) Provisional application No. 61/705,568, filed on Sep. 25, 2012.

(51) Int. Cl.
*G01B 11/30* (2006.01)
*G01N 21/956* (2006.01)

(52) U.S. Cl.
CPC ... *G01N 21/95607* (2013.01); *G01B 2290/30* (2013.01)

(58) Field of Classification Search
CPC ............ G01B 2290/30; G01B 9/02025; G01N 21/95607
See application file for complete search history.

(56) References Cited

U.S. PATENT DOCUMENTS

| 5,818,592 | A | 10/1998 | Womack et al. |
| 7,002,695 | B2 | 2/2006 | Feldman |
| 9,810,643 | B1 * | 11/2017 | Shoham ........... G01N 21/95623 |
| 2009/0284835 | A1 | 11/2009 | Meshulach et al. |

* cited by examiner

*Primary Examiner* — Hwa Andrew Lee
(74) *Attorney, Agent, or Firm* — Lowenstein Sandler LLP

(57) ABSTRACT

A system that may include a radiation source to generate a beam of coherent radiation; traveling lens optics to focus the beam so as to generate multiple spots on a surface of a sample and to scan the spots together over the surface; collection optics to collect the radiation scattered from the multiple spots and to focus the collected radiation so as to generate a pattern of interference fringes; and a detection unit to detect changes in the pattern of interference fringes.

16 Claims, 16 Drawing Sheets

500

700

SYSTEM AND METHOD FOR DEFECT DETECTION USING MULTI-SPOT SCANNING

CROSS-REFERENCE TO RELATED APPLICATIONS

This patent application is a continuation of U.S. Non-Provisional patent application Ser. No. 14/037,304, filed Sep. 25, 2013, which claims the benefit under 35 U.S.C. § 119(e) of U.S. Provisional Patent Application No. 61/705,568, filed Sep. 25, 2012, which are hereby incorporated by reference herein in their entireties.

BACKGROUND

It is known in the art of microscopy to observe phase variations in an image of a sample in order to enhance detection of features that would otherwise be difficult to see. DIC microscopy provides a monochromatic shadow cast image that effectively displays the gradient of optical paths. Those regions of the sample where the optical paths increase along a certain reference direction appear brighter, while those where the path differences decrease appear in reverse contrast. Image contrast is greater the steeper the gradient of path differences. DIC methods are useful for highlighting features such as very thin filaments and sharp interfaces, and show differences in local refractive index, as well as changes in surface elevation.

Traveling lens acousto-optic devices are also known in the art. A device of this sort is described, for example, by Eveleth in U.S. Pat. No. 3,851,951, whose disclosure is incorporated herein by reference. An acoustic transducer is coupled to one end of an acousto-optic Bragg cell. The acoustic transducer generates frequency-modulated acoustic pulses in the Bragg cell, which travel from one end of the cell to the other. The resulting spatial frequency variation of the traveling acoustic pulse causes a laser beam that passes through the pulse area to be focused onto an image plane. As the acoustic pulse travels from one end of the Bragg cell to the other, it acts as a traveling lens, causing the focused laser spot to be scanned across the image plane.

U.S. Pat. No. 7,002,695 of Feldman, which is incorporated herein by reference, teaches of dual spot traveling lens system for optical assessment of a sample.

There is a growing need to provide an efficient system and a method for assessment of a sample.

SUMMARY

According to various embodiments of the invention there may be provided a system that may include a radiation source, adapted to generate a beam of coherent radiation; traveling lens optics, adapted to focus the beam so as to generate first, second and third spots on a surface of a sample and to scan the spots together over the surface; collection optics, positioned to collect the radiation scattered from the first, second and third spots and to focus the collected radiation so as to generate a pattern of interference fringes; and a detection unit, adapted to detect changes in the pattern of interference fringes.

The traveling lens optics comprise an acousto-optic Bragg cell and an acoustic transducer coupled to the cell so as to produce first, second and third frequency-modulated acoustic pulses, which travel along a length of the cell, such that when the beam of radiation passes through the cell, it is focused by the first, second and third pulses so as to generate and scan the first, second and third spots, respectively.

The transducer is controllable so as to vary a relative timing and phase of the acoustic pulses, thereby controlling a spacing and relative phase of the first, second and third spots.

The second spot is formed between the first and third spots; and wherein the traveling lens optics are arranged to generate the first and third spots as being of a same phase and to generate the second spot as being phase shifted from the first and third spots.

The traveling lens optics are arranged to control at least one of a phase and amplitude of each one of the first, second and third spots so as to cause the pattern of interference fringes to remain substantially stationary at a certain optical plane regardless of topographic differences between different portions of the surface of sample.

The collection optics comprises a beam stop which is arranged to block at least one interference fringe of the pattern of interference fringes from impinging on a detector of the detection unit.

The traveling lens optics are arranged to generate at least one additional spot on each side of the first, second and third spots to form an array of spots that comprises more than three spots and wherein all the spots of the array of spot participate in a generation of the pattern of interference fringes.

The second spot is positioned at a center of the array of spots; wherein phases of spots of the array of spots are symmetrical about the second spot.

The traveling lens optics are arranged to vary at least one optical character of at least one spot of the first, second and third spot in alternation while scanning the first, second and third spots over the surface so as to facilitate a generation of multiple images of non-continuous portions of the surface of the sample.

The system may include a processor that is arranged to calculate, in response to the multiple images, a phase and an amplitude of near field radiation in proximity to the surface of the sample.

The processor may be arranged to classify defects of the sample in response to the phase and the amplitude of the near field radiation.

The traveling lens optics are arranged to vary a phase of the at least one spot in alternation between at least three different phase values to generate at least three images, each of the at least three images corresponds to a different phase value.

The traveling lens optics are arranged to modulate at least one optical character of at least one spot of the first, second and third spot during the scanning of the surface of the sample.

The traveling lens optics are arranged to vary a phase different between the second spot and a phase of the third and first spots while maintaining the second spot between the first and third spots.

There may be provided a system that may include a radiation source, adapted to generate a beam of coherent radiation; traveling lens optics, adapted to focus the beam so as to generate multiple spots on a surface of a sample and to scan the multiple spots together over the surface and to vary at least one optical character of at least one spot of the multiple spots in alternation while scanning the multiple spots over the surface; collection optics, positioned to collect the radiation scattered from the multiple spots and to focus the collected radiation so as to generate a pattern of interference fringes; and a detection unit, adapted to detect changes in the pattern of interference fringes and to generate multiple images of non-continuous portions of the surface of the sample, each image of the multiple images is associated with a certain value of the at least one optical character.

The system may include a processor that is arranged to calculate, in response to the multiple images, a phase and an amplitude of near field radiation in proximity to the surface of the sample.

The processor may be arranged to classify defects of the sample in response to the phase and the amplitude of the near field radiation.

The traveling lens optics is arranged to vary a phase of the at least one spot in alternation between at least three different phase values to generate at least three images, each of the at least three images corresponds to a certain phase value.

There may be provided a system that may include illumination optics that comprises a radiation source and a mask, that is arranged to illuminate a surface of a sample with a spot of radiation; collection optics, adapted to collect radiation scattered from the spot and to split the radiation scattered from the spot to form three spots that generate a pattern of diffraction fringes; and a detection unit, adapted to detect changes in the pattern of interference fringes.

There may be provided methods for activating each one of the systems described in the specification. There may be provided a method for each claim or combination of claims.

According to an embodiment of the invention there may be provided method that may include generating, by a radiation source, a beam of coherent radiation; focusing, by traveling lens optics, the beam so as to generate first, second and third spots on a surface of a sample and scanning the spots together over the surface; collecting, by collection optics, the radiation scattered from the first, second and third spots and focusing the collected radiation so as to generate a pattern of interference fringes; and detecting, by a detection unit, changes in the pattern of interference fringes.

According to an embodiment of the invention there may be provided method that may include generating by a radiation source, a beam of coherent radiation; focusing by traveling lens optics, beam so as to generate multiple spots on a surface of a sample; scanning the multiple spots together over the surface while varying at least one optical character of at least one spot of the multiple spots in alternation; collecting, by collection optics, radiation scattered from the multiple spots and focusing the collected radiation so as to generate a pattern of interference fringes; detecting, by a detection unit, changes in the pattern of interference fringes; and generating multiple images of non-continuous portions of the surface of the sample, each image of the multiple images is associated with a certain value of the at least one optical character.

According to an embodiment of the invention there may be provided method that may include illuminating, by illumination optics that comprises a radiation source and a mask, that is arranged to illuminate a surface of a sample with a spot of radiation; collecting, by collection optics radiation scattered from the spot; splitting the radiation scattered from the spot to form three spots that generate a patters of diffraction fringes; and detecting, by a detection unit, changes in the pattern of interference fringes.

Any combinations of any of the components of any of the figures can be provided. Any combination of any of the mentioned above systems can be provided.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof may best be understood by reference to the following detailed description when read with the accompanying drawings in which:

Figure 1:
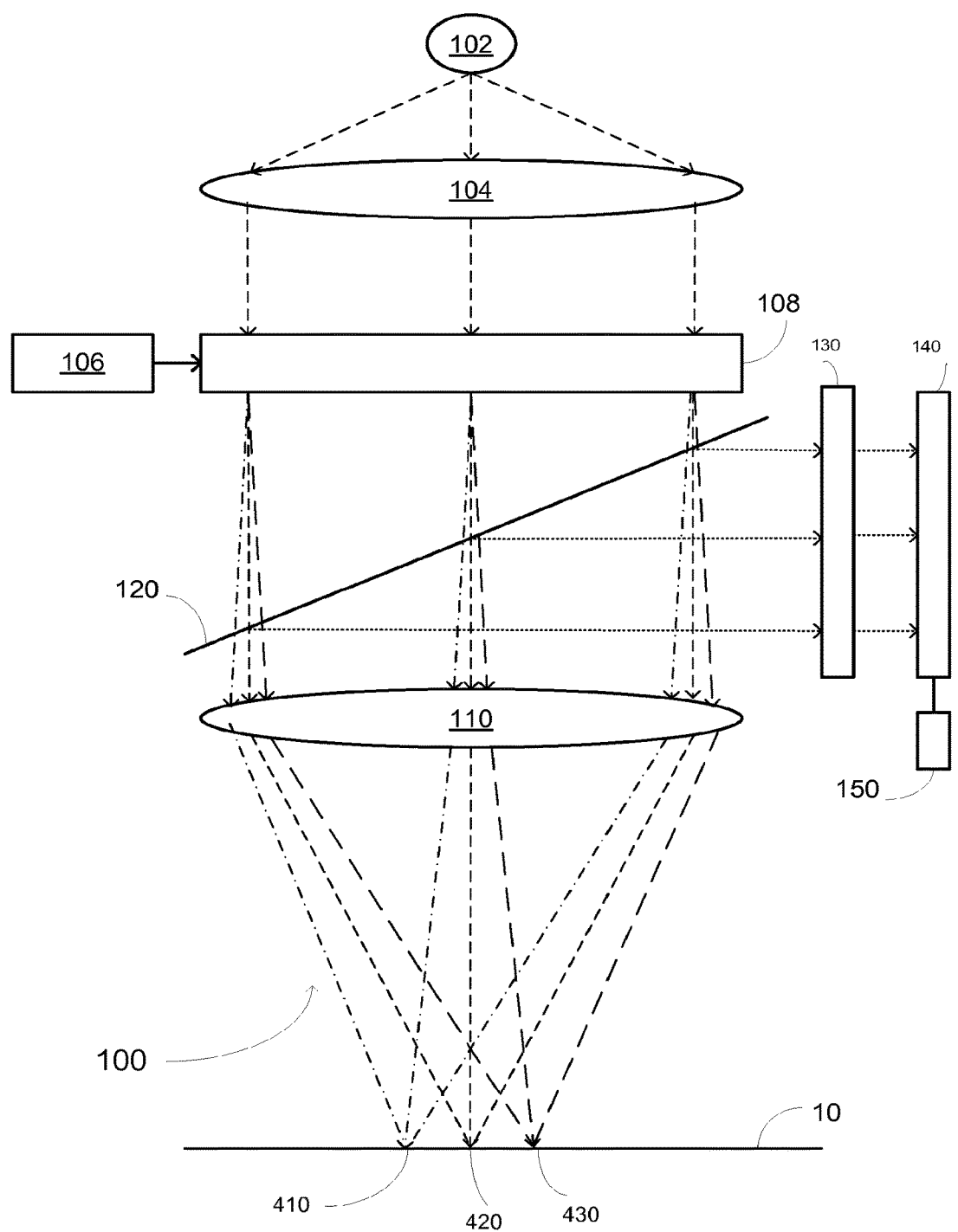
FIG. 1 illustrates a system according to an embodiment of the invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE DRAWINGS

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

Because the illustrated embodiments of the present invention may, for the most part, be implemented using electronic components and modules known to those skilled in the art, details will not be explained in any greater extent than that considered necessary as illustrated above, for the understanding and appreciation of the underlying concepts of the present invention and in order not to obfuscate or distract from the teachings of the present invention.

Embodiments of a system that uses three or more spots will now be discussed in more detail.

FIG. 1 illustrates a system 100 according to an embodiment of the invention.

System 100 may be integrated with, or be part of one or more computer systems (e.g., a server machine, a personal computer, a workstation, etc.) and can include:

1. a radiation source 102,
2. collimating lens 104 for collimating radiation from the radiation source 102,
3. traveling lens optics that includes transducer 106 and acousto-optic Bragg cell 108,
4. beam splitter 120,
5. objective lens 110,
6. a detection unit that includes a beam stop 130 and detector 140; and
7. a processor 150.

In addition, system 100 can include components (e.g., one or computer programs or application modules) that cause processor 150 to perform operations described herein.

The objective lens 110 and the beam splitter 120 belong to the illumination optics and to the collection optics of the system 100.

The radiation source 102 is adapted to generate a beam of coherent radiation.

The traveling lens optics is adapted to focus the beam so as to generate first, second and third spots 410, 420 and 430 on a surface of sample 10 and to scan the spots (410, 420 and 430) together over the surface.

The collection optics is positioned to collect the radiation scattered from the first, second and third spots 410, 420 and 430 and to focus the collected radiation so as to generate a pattern of interference fringes at a Fourier plane in which the beam stop 130 is positioned.

The detection unit is adapted to detect changes in the pattern of interference fringes.

Figure 2:
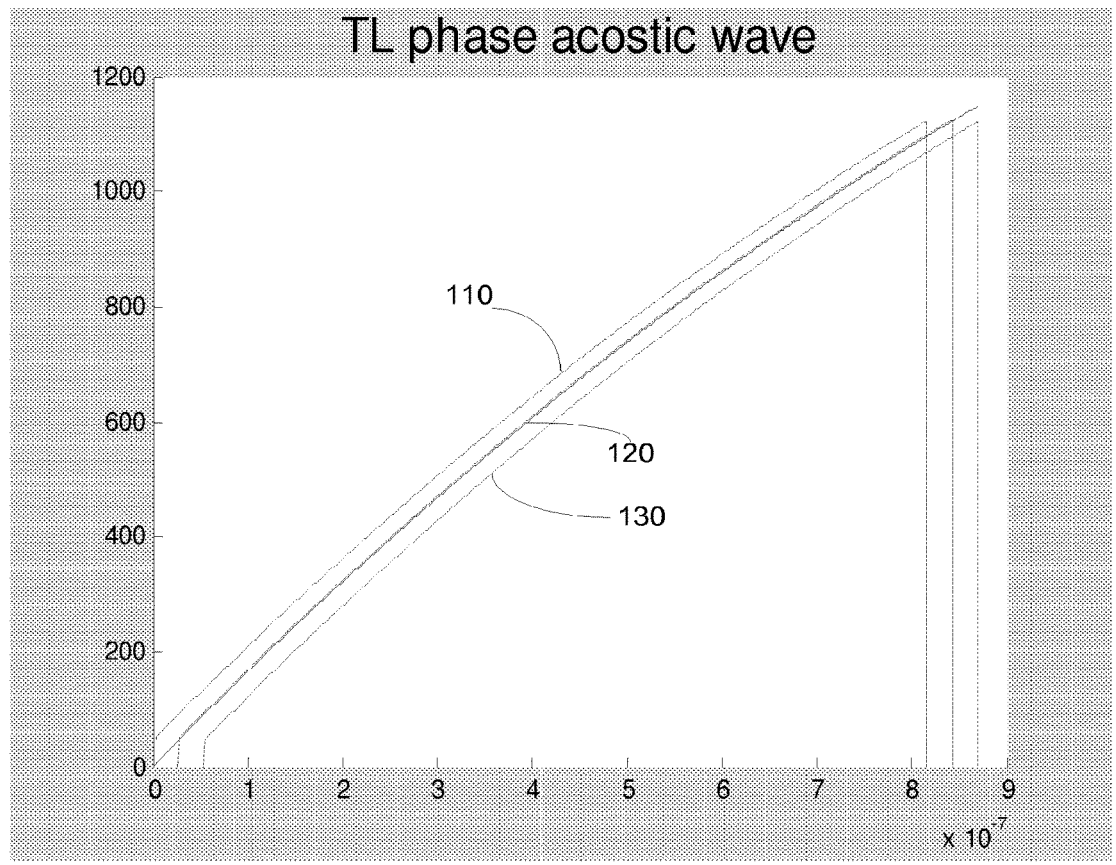
FIG. 2 illustrates three irradiation signals according to an embodiment of the invention.

The acoustic transducer 106 is arranged to irradiate the acousto-optic Bragg cell 108 by irradiation signals such as step-shaped time-shifted first, second and third frequency-modulated acoustic pulses. FIG. 2 illustrates three irradiation signals according to an embodiment of the invention.

These irradiation signals can include step-shaped time-shifted first, second and third frequency-modulated acoustic pulses 110, 120 and 130 respectively.

Figure 3:
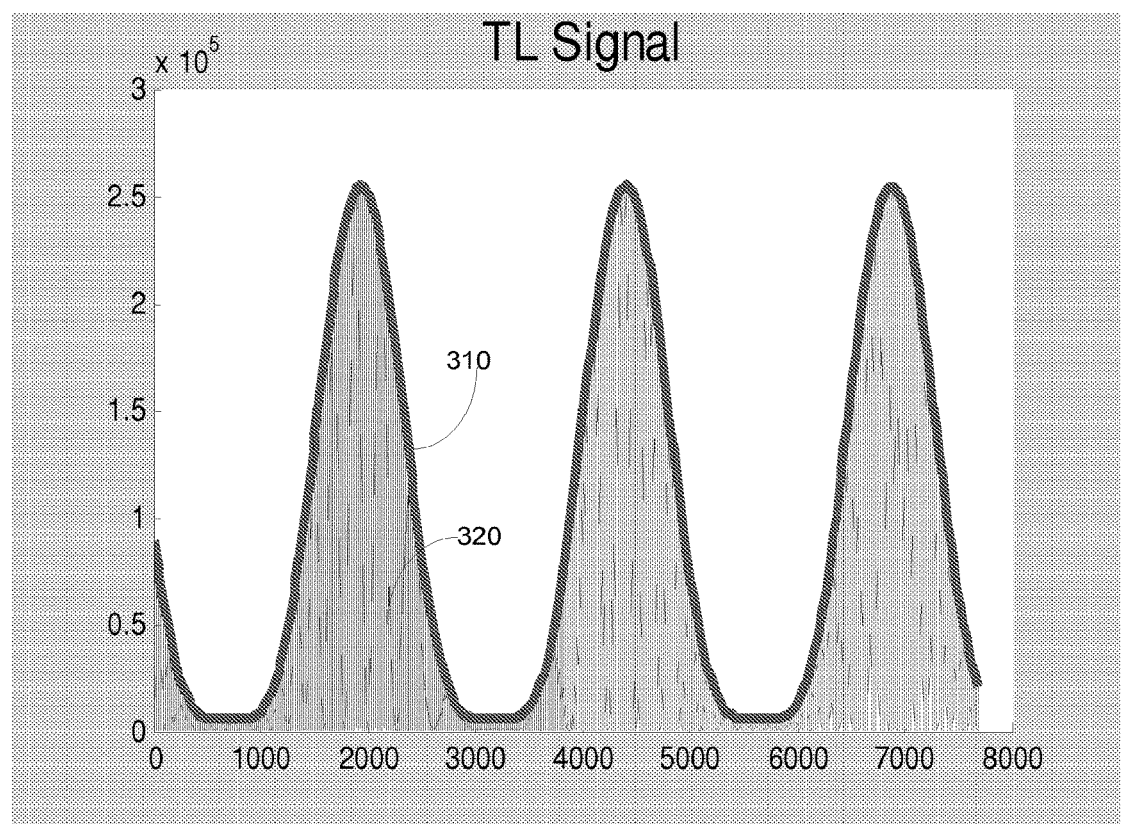
FIG. 3 illustrates a superposition of the three irradiation signals that are provided to an acousto-optic Bragg cell according to an embodiment of the invention.

The first, second and third frequency-modulated acoustic pulses may interfere to generate a high frequency sinusoidal signal that has an envelope that includes first, second and third peaks. FIG. 3 illustrates a superposition of the three irradiation signals that are provided to an acousto-optic Bragg cell according to an embodiment of the invention. As shown, a high frequency sinusoidal signal 320 has an envelope 310 that includes first, second and third peaks.

Figure 4:
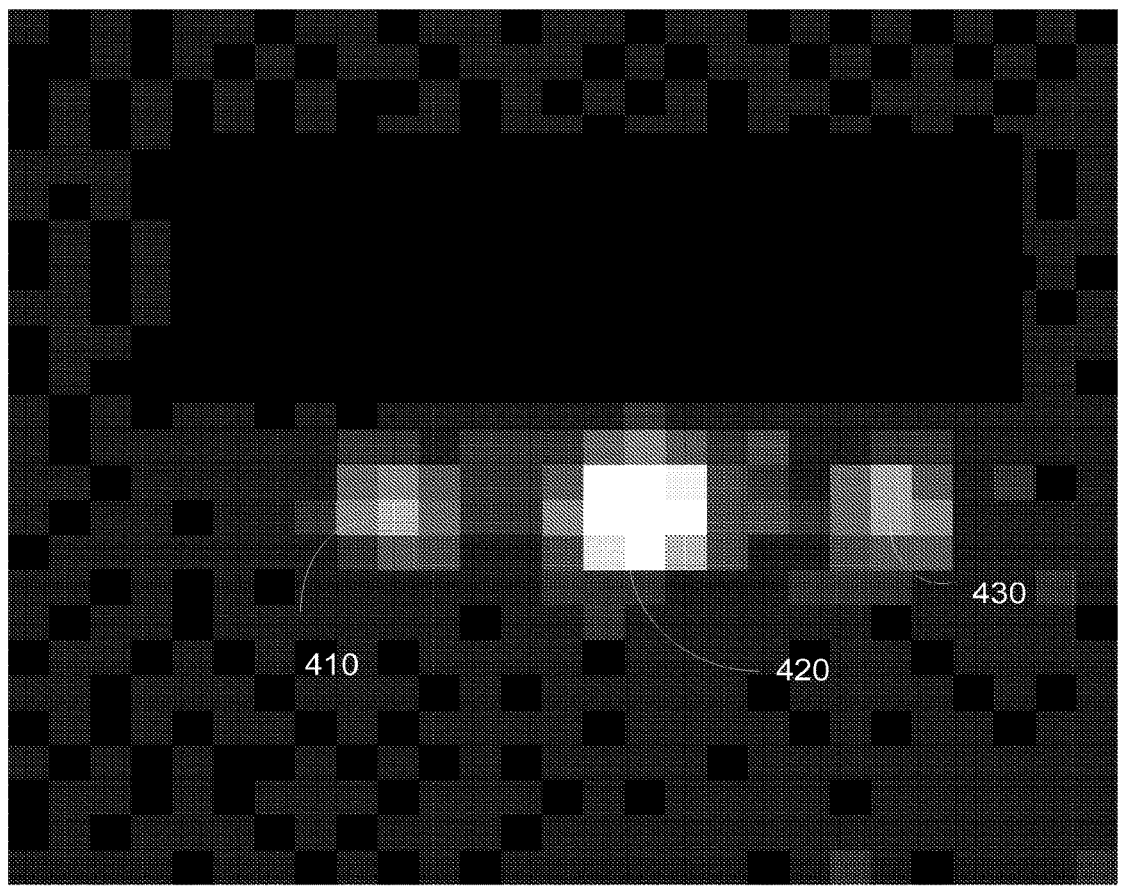
FIG. 4 illustrates three spots that are formed on a surface of a sample according to an embodiment of the invention.

These irradiation signals can produce first, second and third frequency-modulated acoustic pulses, which travel along a length of the acousto-optic Bragg cell 108, such that when the beam of radiation passes through the acousto-optic Bragg cell 108, it is focused by the first, second and third pulses so as to generate and scan the first, second and third spots. FIG. 4 illustrates spots that are formed on a surface of a sample according to an embodiment of the invention. As shown in FIG. 1 and FIG. 4, the spots include first spot 410, second spot 420 and third spot 430.

It is noted that the transducer 106 can generate irradiation signals of different amplitude, phase, shape and relative time shifts.

The transducer 106 may be controllable (for example by a controller—not shown) so as to vary a relative timing and phase of the acoustic pulses, thereby controlling a spacing and relative phase of the first, second and third spots 410, 420 and 430. Larger spacing between spots can be obtained by increasing the time shift between the formation of the spots.

According to an embodiment of the invention, the system 100 can be robust and can use fixed beam stops by having a traveling lens optics that is arranged to control at least one of a phase and an amplitude of each one of the first, second and third spots so as to cause the pattern of interference fringes to remain substantially stationary (at a Fourier plane in which the beam stop 130 is located) regardless of topographic differences between different portions of the surface of sample. Thus, changes in phase introduced by defects of structural elements of the sample will not change the location of the fringes of interference but may change their amplitude.

Such a robust system 100 can be obtained when the traveling lens optics is arranged to generate the first and third spots as being of a same phase and to generate the second spot as being phase shifted from the first and third spot.

According to an embodiment of the invention, different phases may change the intensities of the different interference fringes but may not change the overall energy included in the entire interference pattern.

The detector 140 may detect at each point in time the overall energy of a pattern of interference fringes. The beam stop 130 can mask some of the interference fringes and can allow some interference fringes to reach the detector 140 and thus allows the detector 140 to distinguish between signals obtained at different situations (for example—defect and defect free situations).

Figure 5:
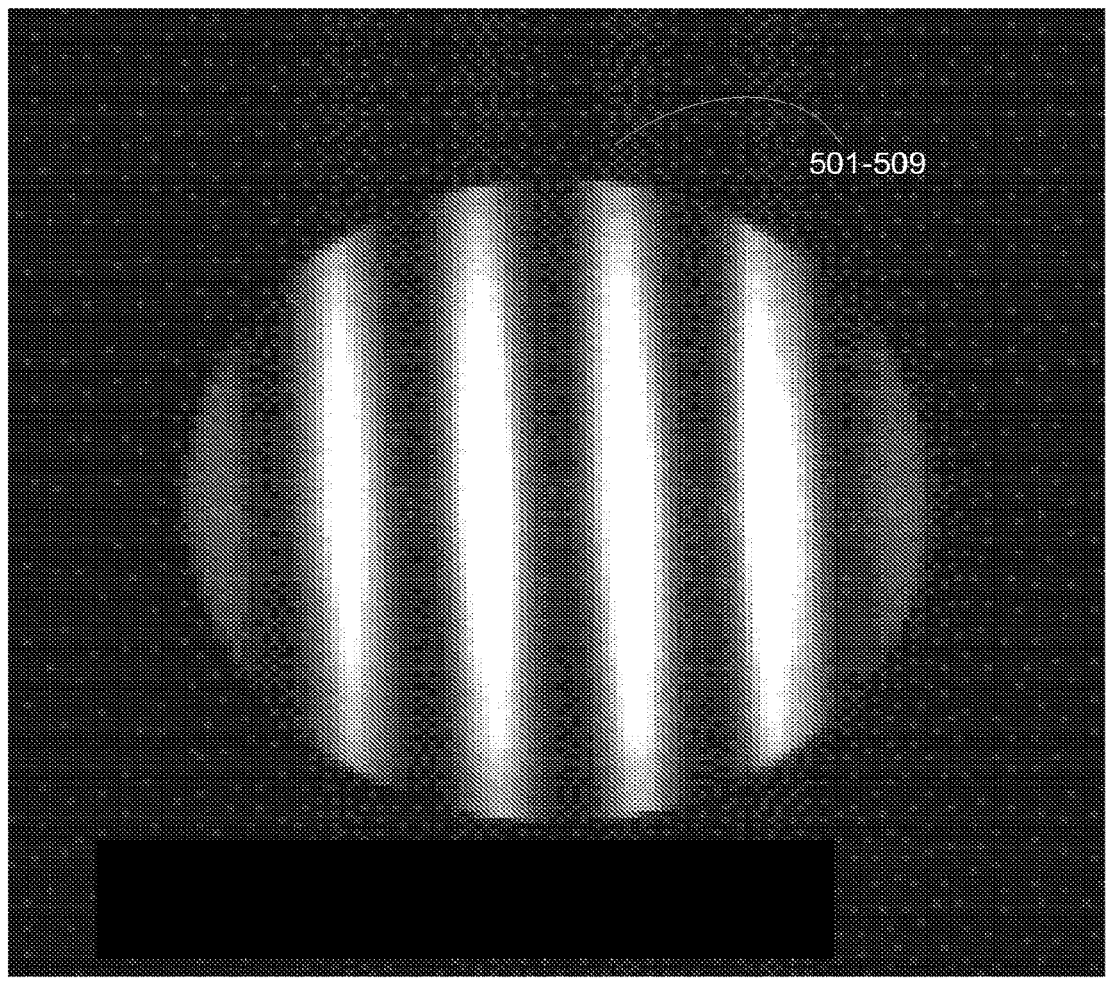
FIG. 5 illustrates a pattern of interference fringes formed at a Fourier plane according to an embodiment of the invention.

FIG. 5 illustrates an example pattern 500 of interference fringes that includes nine interference fringes 501-509—five dark fringes and four white fringes that are arranged in an interlaced manner, in accordance with some embodiments.

Figure 6:
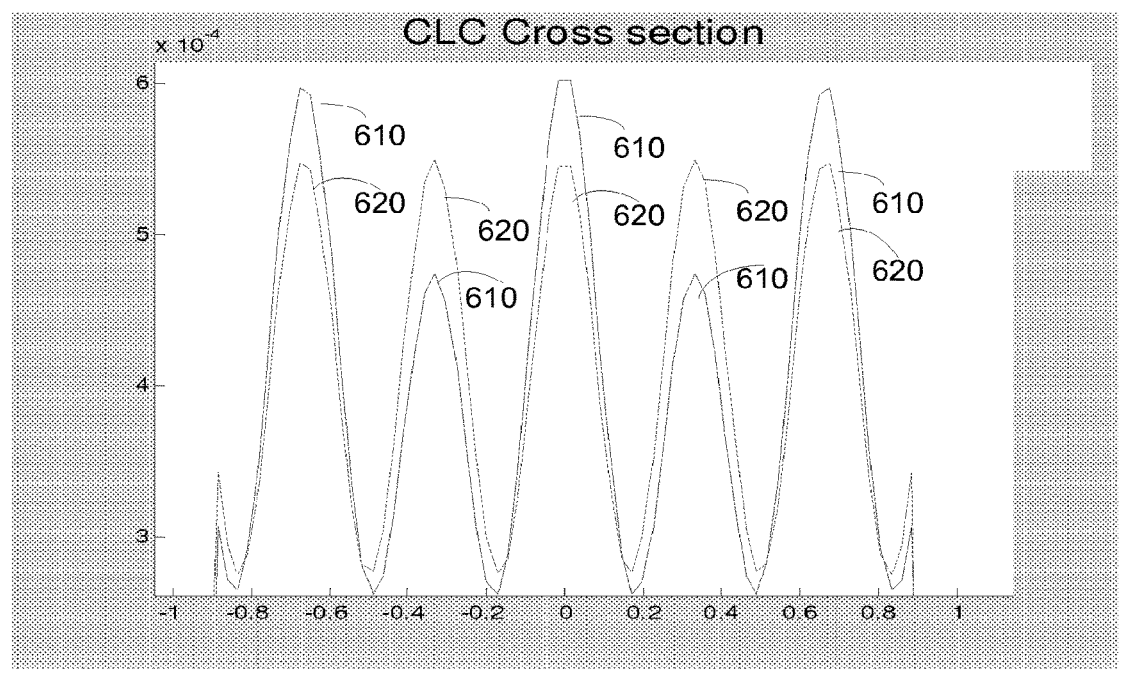
FIG. 6 illustrates a cross sectional view of intensities of a first pattern of interference fringes formed at a Fourier plane as a result of a defect and a second pattern of interference fringes formed at the Fourier plane as a result of an illumination of a defect free point of the surface of the sample according to an embodiment of the invention.

FIG. 6 illustrates a sample cross sectional view of intensities of a first pattern 610 of interference fringes formed at a Fourier plane as a result of a defect and a second pattern 620 of interference fringes formed at the Fourier plane as a result of an illumination of a defect free point of the surface of the sample according to an embodiment of the invention. The interference fringes have an elongated oval shape and the cross section is taken along their traverse axes.

As can be seen from FIG. 6, the overall energy of first pattern 610 and second pattern 620 may be the same.

The first, fifth and ninth interference fringes of first pattern 610 can be stronger than the first, fifth and ninth interference fringes of the second pattern 620.

The third and seventh interference fringes of first pattern 610 can be weaker than the third and seventh interference fringes of the second pattern 620.

The beam stop 130 may increase the sensitivity of defect detection by masking the first, fifth and ninth interference fringes, by blocking all interference fringes but one or more of the first, fifth and ninth interference fringes, by masking the third and seventh interference fringes, by blocking all interference fringes but one or more of the third and seventh interference fringes, and the like.

Figure 7:
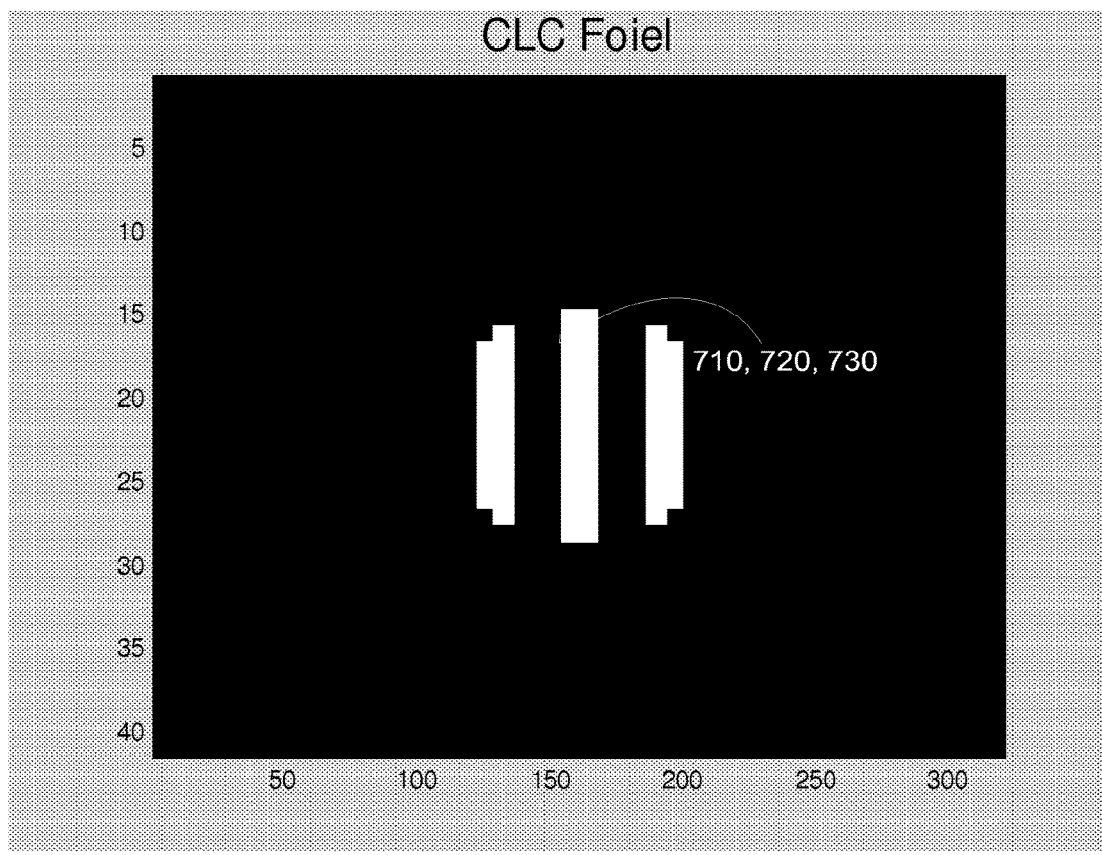
FIG. 7 illustrates a beam stop that has apertures that allow the passage of only some of the interference fringes of the pattern according to an embodiment of the invention.

FIG. 7 illustrates an example beam stop 130 as including three apertures 710, 720 and 730 that block all interference fringes except the first, fifth and ninth interference fringes, in accordance with some embodiments.

Although some of the figures illustrate the formation of three spots, the system may be arranged to generate an array of more than three spots. For example—it may scan the surface of the sample 10 with an array (for example—linear array) of spots that may include an uneven number of spots that exceeds three. All the spots of the array are close enough to each other to participate in a generation of the pattern of interference fringes.

It is further noted that the system 100 may generate multiple arrays of spots, wherein the arrays are distance from each other such as not to influence each other.

The array of spot can be formed such that the location of the pattern of interference fringes will remain substantially stationary at a certain optical plane (such as the Fourier plane in which the beam stop 130 is located) regardless of topographic differences between different portions of the surface of sample. Thus, changes in phase introduced by defects of structural elements of the sample will not change the location of the fringes of interference but may change their amplitude.

Embodiments of a system that scans a sample in an alternating manner will now be discussed in more detail.

It can be very beneficial to reconstruct both the phase and the amplitude of a near field radiation in proximity to the surface of the sample. This reconstruction can provide phase and amplitude information that can assist in classifying defects or otherwise provide better estimation of the surface of the sample.

In this embodiment the processor 150 may be operable (using a respective component such as an application or a module) to calculate, in response to the multiple images, a phase and an amplitude of near field radiation in proximity to the surface of the sample. The calculation can include generating one or more difference images by subtracting one image from another.

The processor 150 may be further operable (using a respective component such as an application or a module) to classify defects of the sample in response to the phase and the amplitude of the near field radiation.

According to an embodiment of the invention, system 100 and especially the traveling lens optics may be arranged to vary at least one optical character of at least one spot of the first, second and third 410, 420 and 430 spot in alternation while scanning the first, second and third spots over the surface so as to facilitate a generation of multiple images of non-continuous portions of the surface of the sample.

Figure 8:
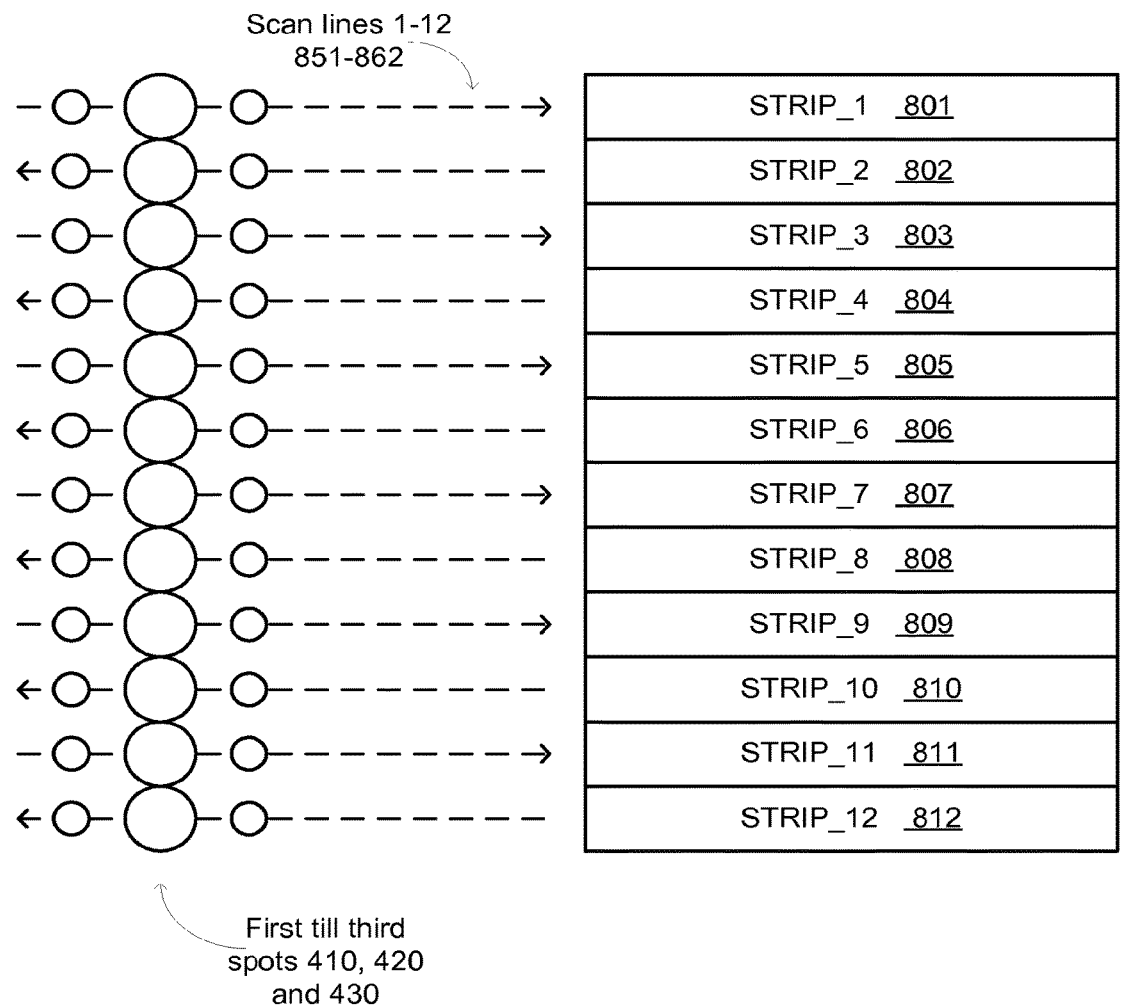
FIG. 8 illustrates multiple scan lines of a raster scan pattern and multiple strips acquired by a detector when the system changes, in an alternating manner, one or more optical characteristics of one or more spots according to an embodiment of the invention.

FIG. 8 illustrates an example system that scans the surface of the sample 10 by a raster scan pattern while alternating between four sets of optical characteristics—such as a phase difference between the phase of the first and third spots and the phase of the second spot, in accordance with some embodiments. It is noted that these sets may differ by amplitude or by other phase differences between the first second and third spots. It is noted that other scanning patterns can be applied.

It is noted that the number of different sets can differ from four and the like. For example, the traveling lens optics are arranged to vary a phase of the at least one spot in alternation between at least three different phase values to generate at least three images, each of the at least three images corresponds to a different phase value.

In these four sets the phase differences may be zero, ninety degrees, one hundred and eighty degrees and two hundred and seventy degrees—but other phase differences can be applied.

When such phase differences are applied, the processor can generate two difference images by subtracting images that were acquired by applying phase differences that differ by 180 degrees from each other.

Referring back to FIG. 4—twelve scan lines 1-12 851-862 are illustrated during which twelve strips 801-812 are obtained.

During each scan line the optical characteristics of the three spots remain unchanged and changes in introduced between scan line. The system alternates between the four sets of optical characteristics so that the first, fifth and ninth strips 801, 805 and 809 are acquired by using a first set of optical characteristics, the second, sixth and tenth strips 802, 806 and 810 are acquired by using a second set of optical characteristics, the third, seventh and eleventh strips 803, 807 and 811 are acquired by using a third set of optical characteristics, and the fourth, eighth and twelfth strips 804, 808 and 812 are acquired by using a forth set of optical characteristics. The first, second, third and fourth set differ from each other.

Strips that are acquired by the same sets of optical characteristics can form an image and strips that are acquired by different sets of optical characteristics can form different images. Each image can be of a non-consecutive portion of the surface of the sample 10. These images can be spatially shifted from each other by a pixel or sub-pixel and can be compared to each other (by using known defect detection algorithms such as die to die, cell to cell comparison algorithms) after performing a registration or alignment process.

Figure 9:
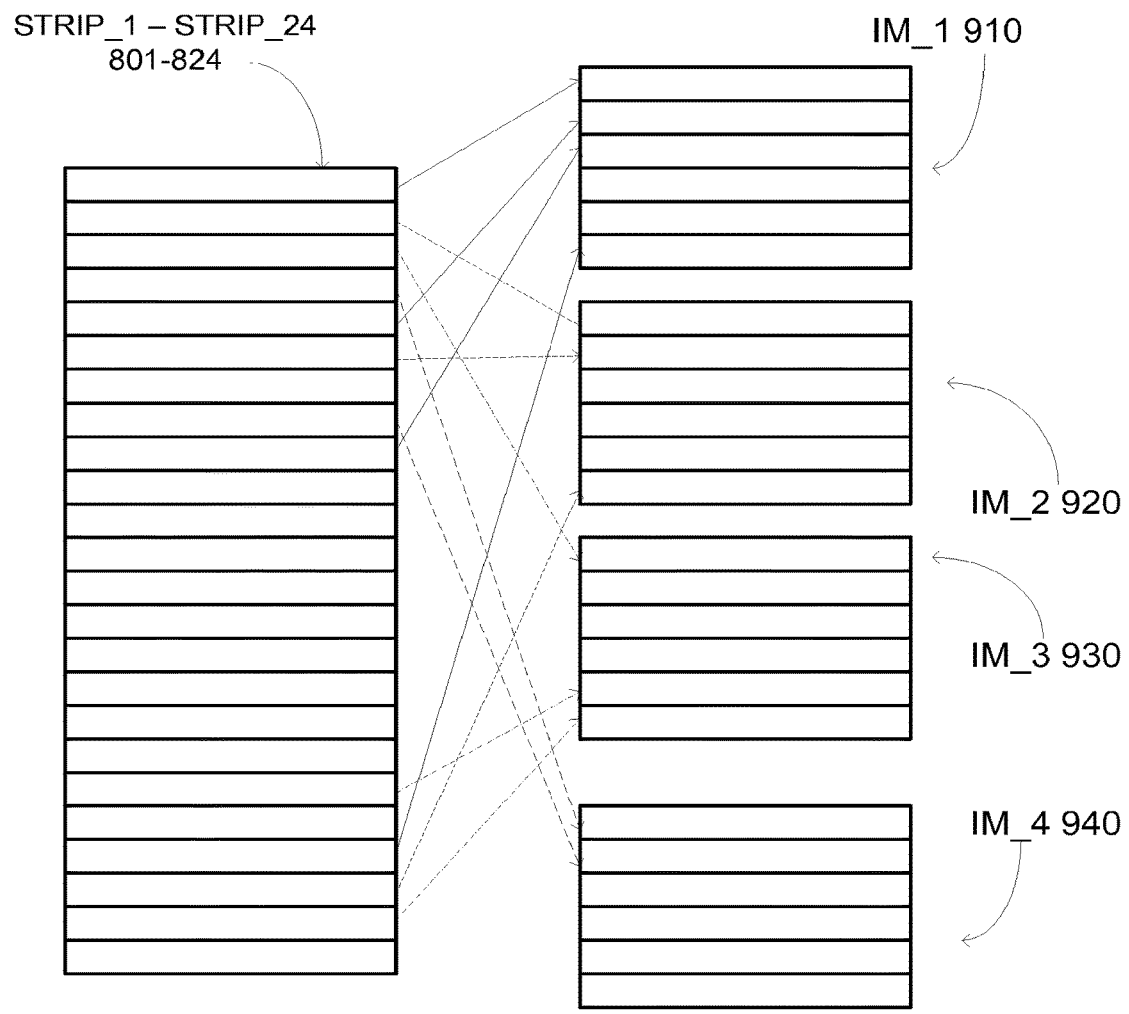
FIG. 9 illustrates a generation of images of non-consecutive portions of the surface of the sample from multiple strips according to an embodiment of the invention.

FIG. 9 illustrates twenty four stripes 801-824 acquired using four alternating sets of optical characteristics, in accordance with some embodiments. The stripes 801-824 can form four images IM_1-IM_4 910-940, where each image includes six strips, in accordance with some embodiments.

Figure 10:
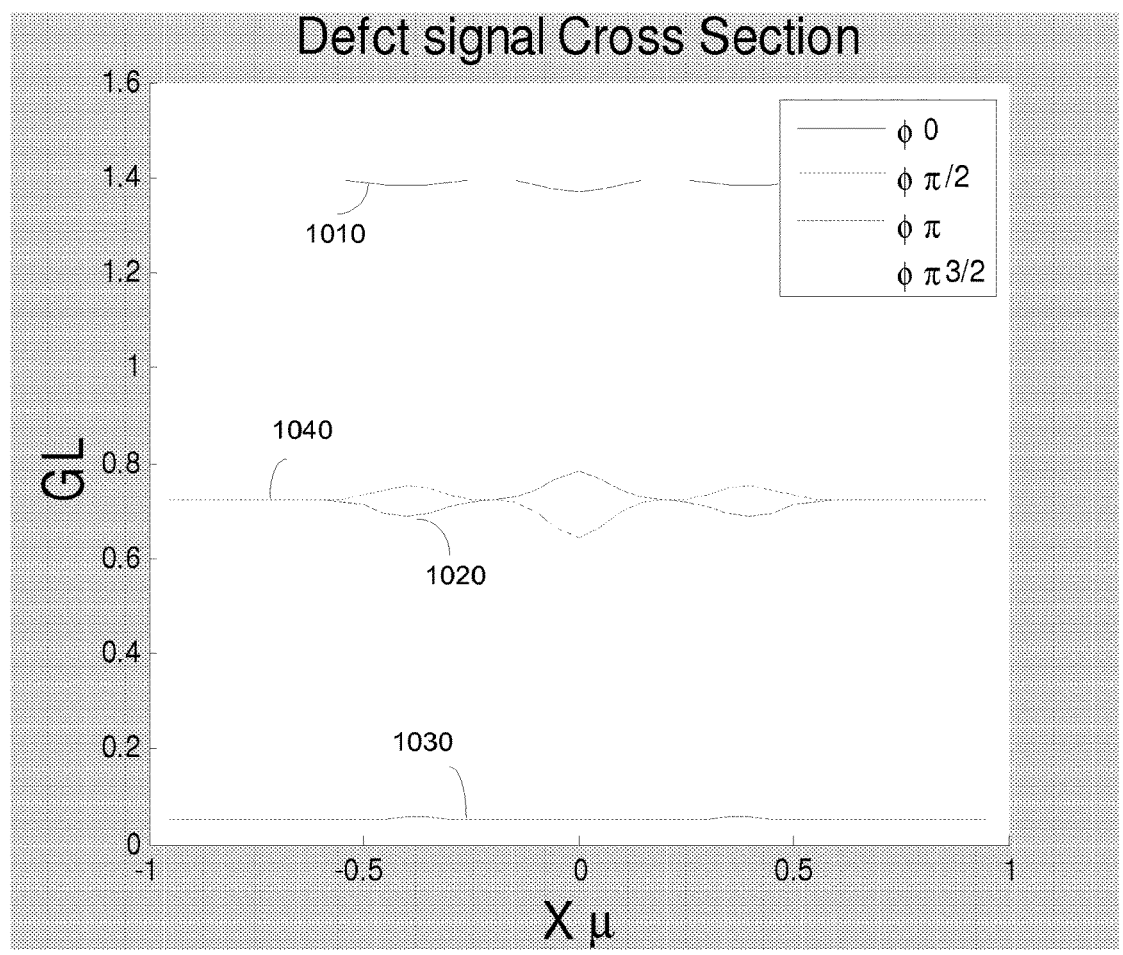
FIG. 10 illustrates defect signal cross sections obtained at different values of optical characteristics according to an embodiment of the invention.

FIG. 10 illustrates defect signal cross section obtained at different values of optical characteristics—curves 1010, 1020, 1030 and 1040 illustrate a cross section of defect signal obtained at phase shifts (between central spot and side spots) of zero, ninety, one hundred and ninety and two hundred and seventy degrees respectively, in accordance with some embodiments.

According to an embodiment of the invention, the system 100 may scan the surface of the sample 10 in an alternating manner by two or more spots.

A system as described above may reconstruct the phase and amplitude of the near field radiation in a manner that is more robust than phase contrast systems that apply two concentric beams of light and are very sensitive to optics defects and aberration—as these different beams propagate through different portions of the pupil—while the system illustrated above the different beams propagate through the same location of the pupil.

Figure 11:
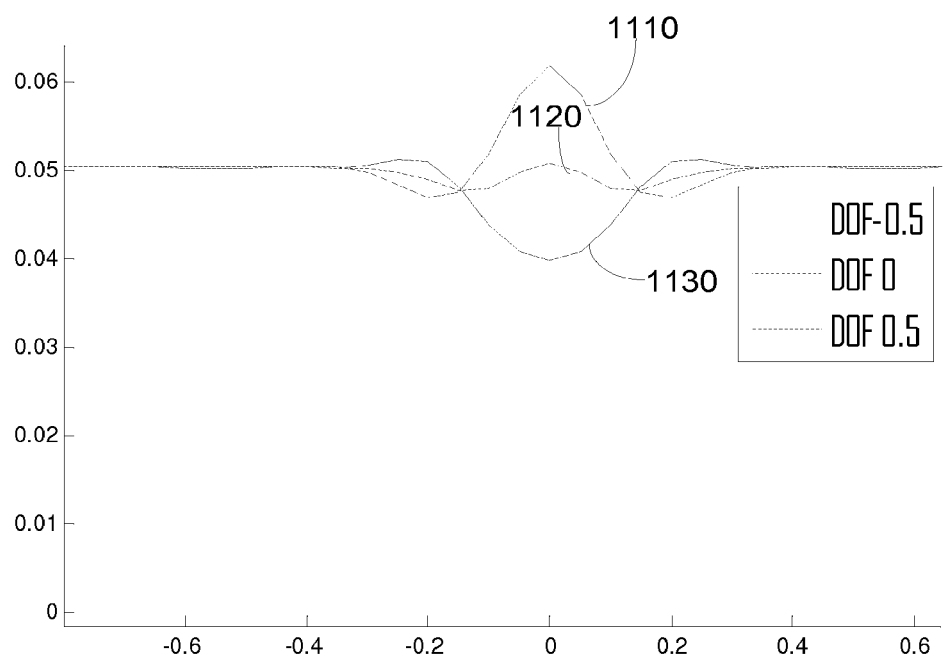
FIG. 11 illustrates detection signals of a prior art phase contrast system at different focus conditions.

FIG. 11 illustrates the difference in detection signals 1110, 1120 and 1130 resulting from focus changes, in accordance with some embodiments. These differences include amplitude and phase changes—especially the center of each curve.

Figure 12:
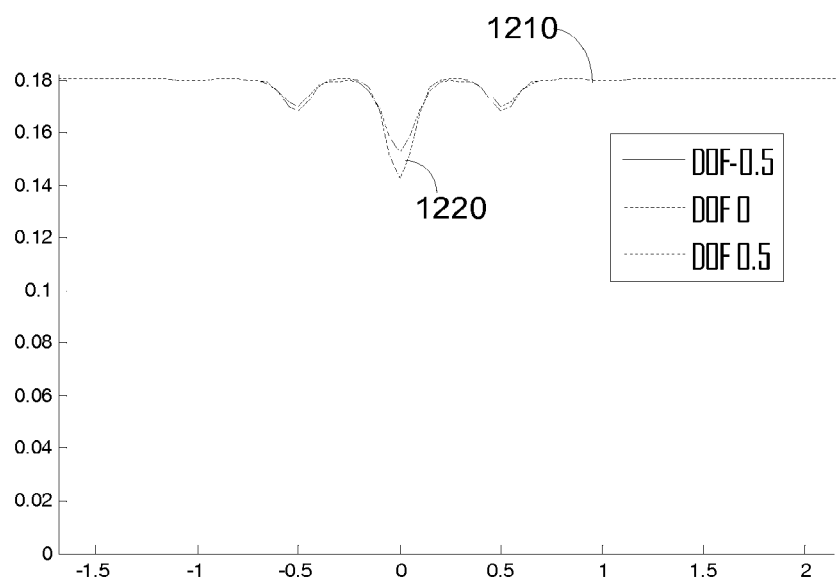
FIG. 12 illustrates detection signals obtained at different focus conditions using the system according to an embodiment of the invention.

FIG. 12 illustrates insignificant differences between detection signals 1210 and 1220 that are obtained by the system 100 at different focal conditions, in accordance with some embodiments.

Figure 13:
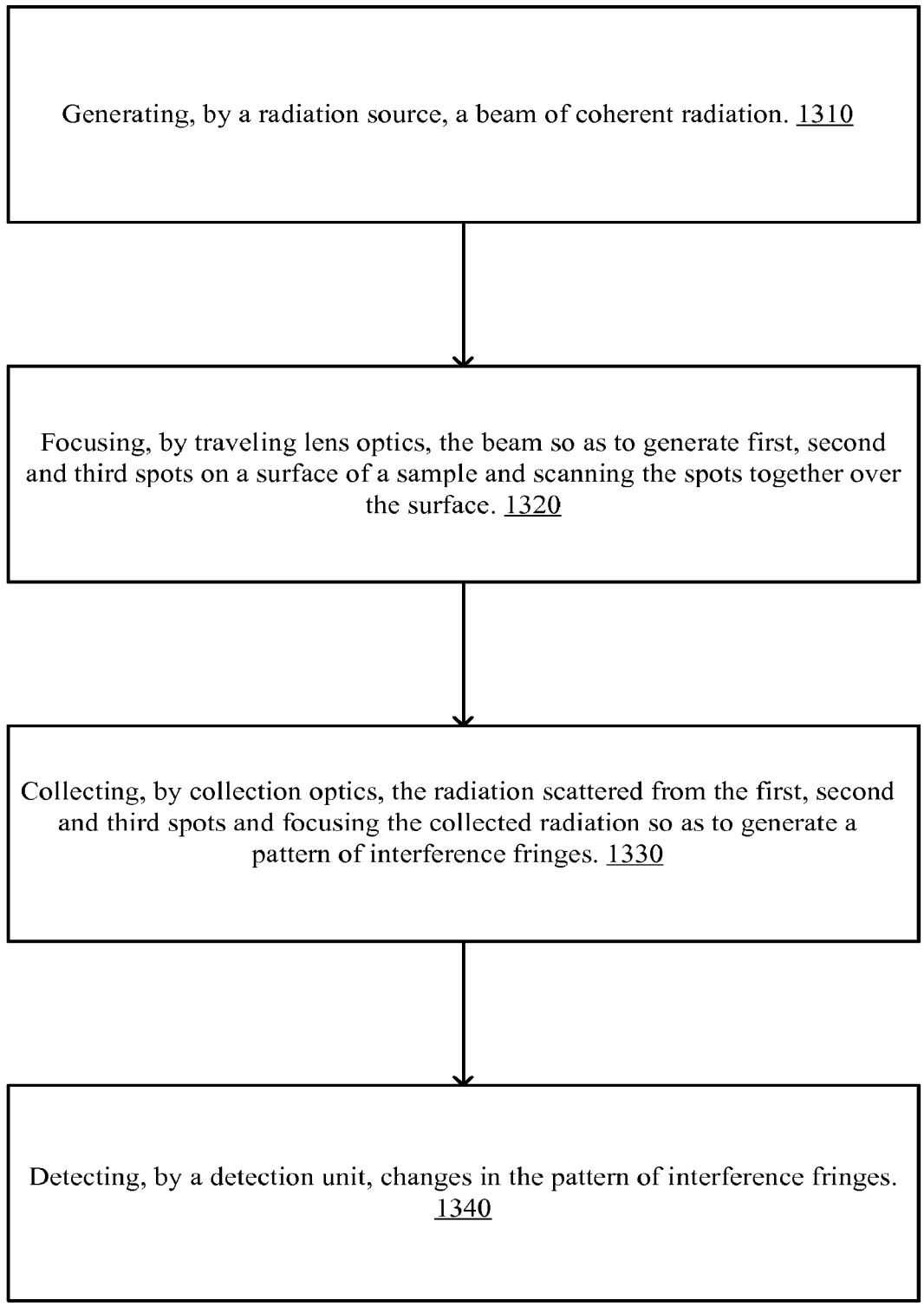
FIG. 13 illustrates a method according to an embodiment of the invention.
Figure 14:
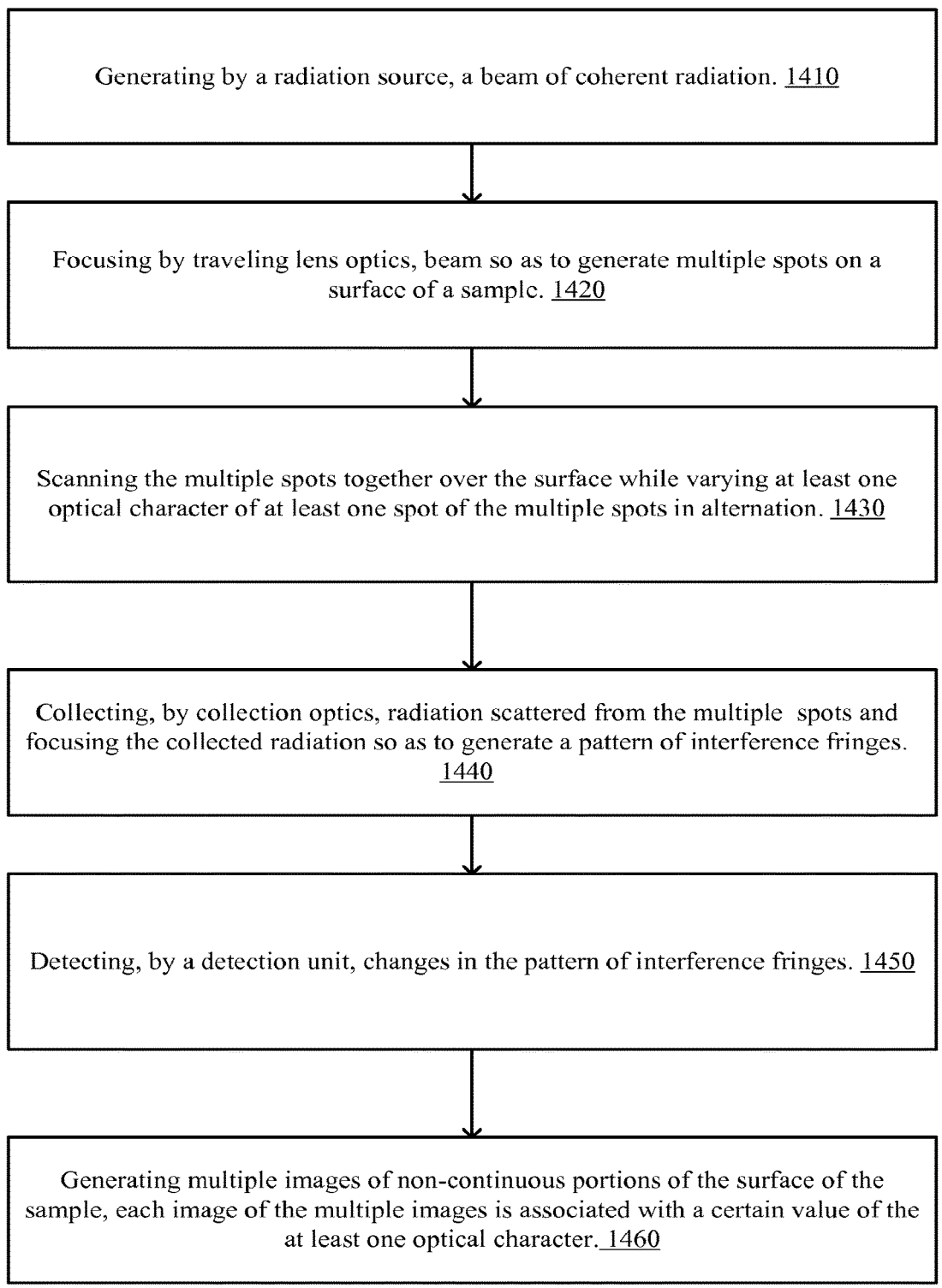
FIG. 14 illustrates a method according to an embodiment of the invention.

Any of the mentioned systems can apply a method according to various embodiment of the invention. FIG. 13 and FIG. 14 illustrate sample methods 1300 and 1400 according to various embodiments of the invention. The methods 1300 and 1400 may be performed by processing logic that comprises hardware (e.g., circuitry, dedicated logic, programmable logic, microcode, etc.), software (e.g., instructions run on a processing device to perform hardware simulation), or a combination thereof.

For simplicity of explanation, the methods of this disclosure are depicted and described as a series of acts. However, acts in accordance with this disclosure can occur in various orders and/or concurrently, and with other acts not presented and described herein. Furthermore, not all illustrated acts may be required to implement the methods in accordance with the disclosed subject matter. In addition, those skilled in the art will understand and appreciate that the methods could alternatively be represented as a series of interrelated states via a state diagram or events. Additionally, it should be appreciated that the methods disclosed in this specification are capable of being stored on an article of manufacture to facilitate transporting and transferring such methods to computing devices. The term "article of manufacture," as used herein, is intended to encompass a computer program accessible from any computer-readable device or storage media. In some implementations, methods 1300 and 1400 may be performed by system 100 of FIG. 1.

Method 1300 may include: generating (1310), by a radiation source, a beam of coherent radiation; focusing (1320), by traveling lens optics, the beam so as to generate first, second and third spots on a surface of a sample and scanning the spots together over the surface; collecting (1330), by collection optics, the radiation scattered from the first, second and third spots and focusing the collected radiation so as to generate a pattern of interference fringes; and detecting (1340), by a detection unit, changes in the pattern of interference fringes.

Method 1400 may include generating (1410) by a radiation source, a beam of coherent radiation; focusing (1420) by traveling lens optics, beam so as to generate multiple spots on a surface of a sample; scanning (1430) the multiple spots together over the surface while varying at least one optical character of at least one spot of the multiple spots in alternation; collecting (1440), by collection optics, radiation scattered from the multiple spots and focusing the collected radiation so as to generate a pattern of interference fringes; detecting (1450), by a detection unit, changes in the pattern of interference fringes; and generating (1460) multiple images of non-continuous portions of the surface of the sample, each image of the multiple images is associated with a certain value of the at least one optical character.

Figure 15:
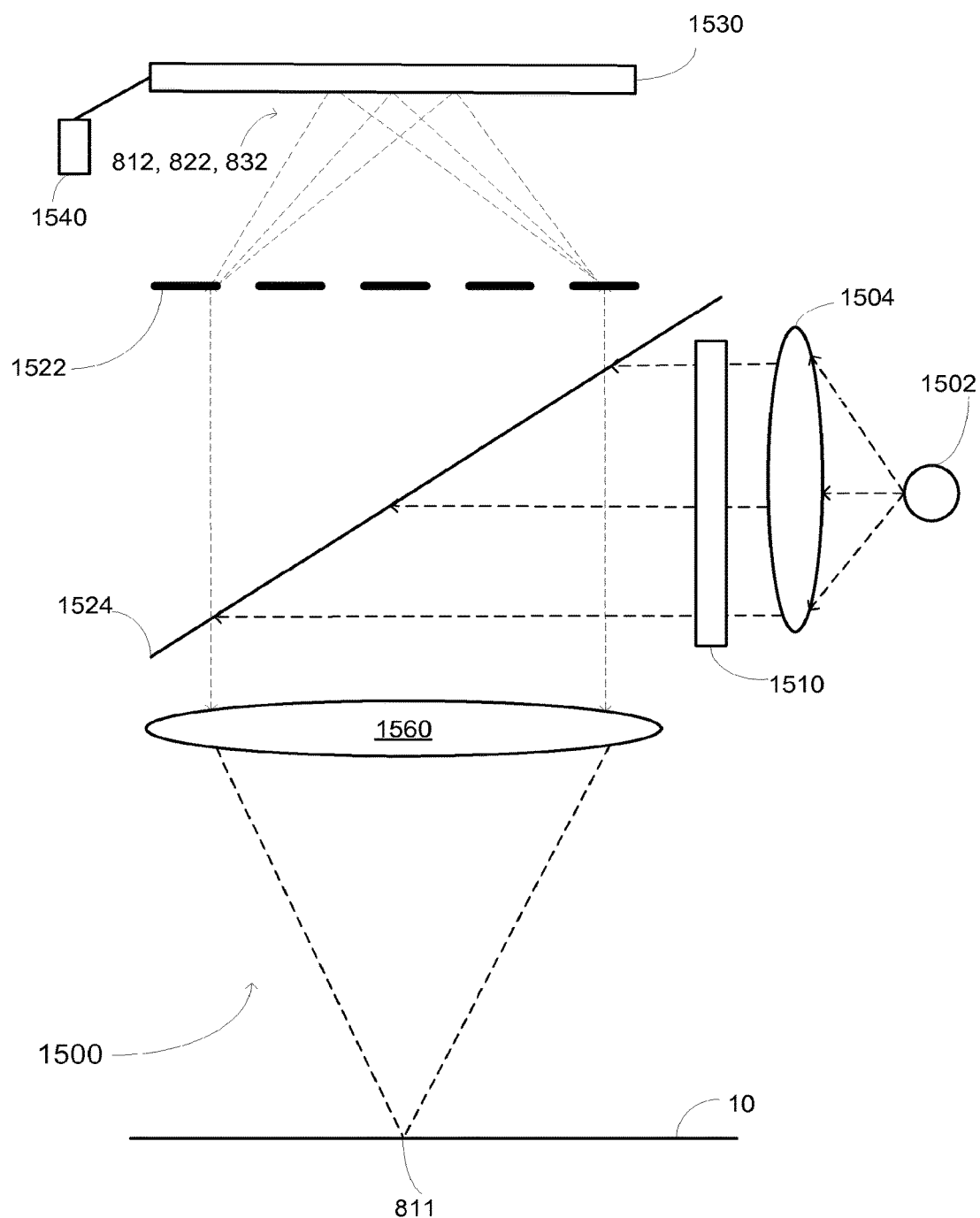
FIG. 15 illustrates a system according to an embodiment of the invention.

FIG. 15 illustrates system 1500 according to an embodiment of the invention.

System 1500 may include: (a) illumination optics that may include a radiation source 1502 and a mask 1510, the illumination optics may be arranged to illuminate a surface of a sample 10 with a spot of radiation 811; (b) collection optics, adapted to collect radiation scattered from the spot and to split (for example—by a grating 1522) the radiation scattered from the spot to form three spots 812, 822 and 832 that generate a pattern of diffraction fringes; and a detection unit that includes detector 1530, adapted to detect changes in the pattern of interference fringes. FIG. 15 also includes beam splitter 1524 and collimating lens 1504. System 1500 also includes processor 1540 operable to process the detection signals provided by the detection unit (using one or more respective components such as one or more applications or modules).

Figure 16:
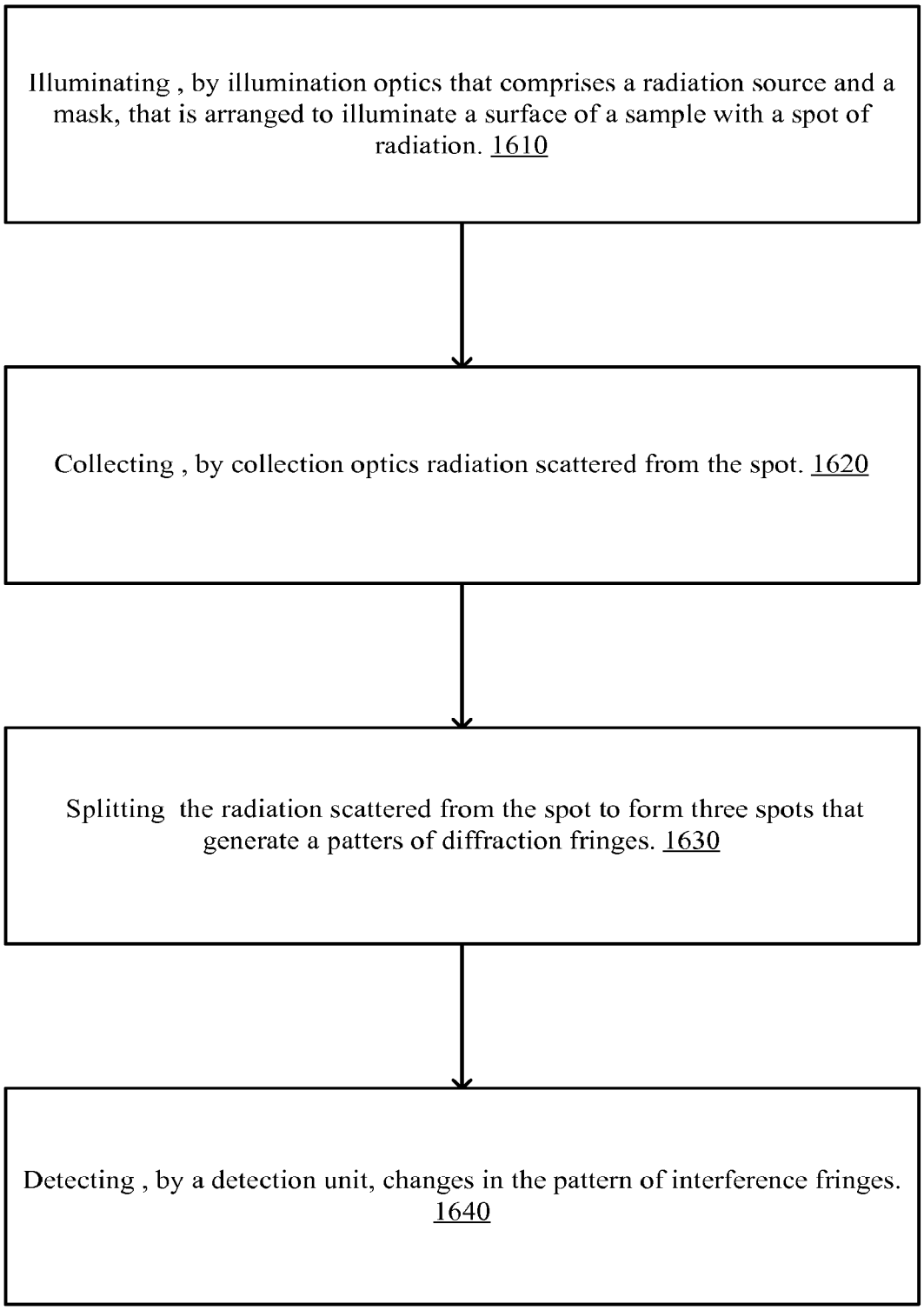
FIG. 16 illustrates a method according to an embodiment of the invention.

FIG. 16 illustrates method 1600 according to an embodiment of the invention. The method 16 may be performed by processing logic that comprises hardware (e.g., circuitry, dedicated logic, programmable logic, microcode, etc.), software (e.g., instructions run on a processing device to perform hardware simulation), or a combination thereof. In some implementations, method 1600 may be performed by system 1500 of FIG. 15.

Method 1600 may include illuminating (1610), by illumination optics that comprises a radiation source and a mask, that is arranged to illuminate a surface of a sample with a spot of radiation; collecting (1620), by collection optics radiation scattered from the spot; splitting (1630) the radiation scattered from the spot to form three spots that generate a patters of diffraction fringes; and detecting (1640), by a detection unit, changes in the pattern of interference fringes.

The assignment of the same reference numbers to various components may indicate that these components are similar to each other.

Figure 17:
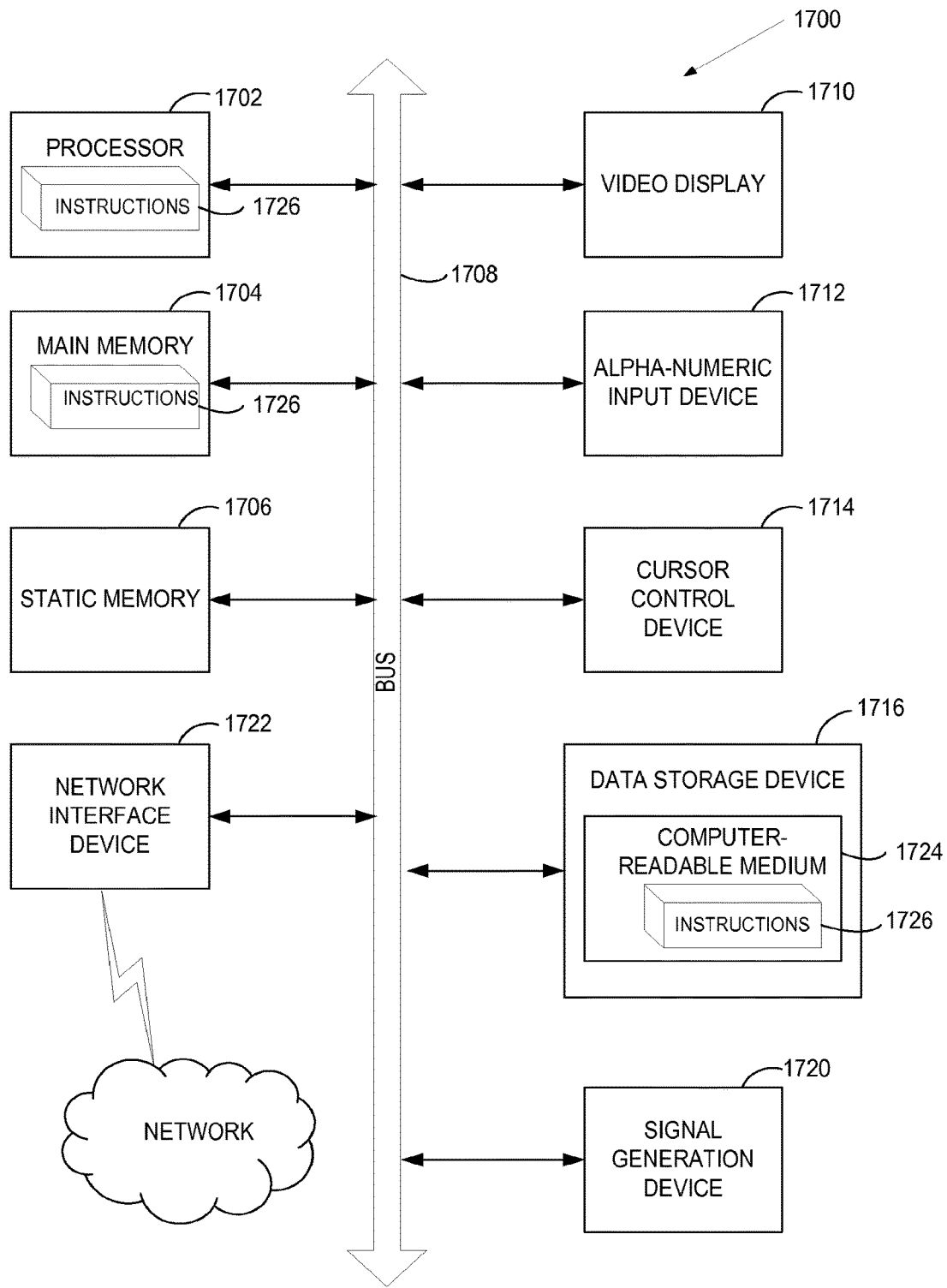
FIG. 17 depicts a block diagram of an illustrative computer system operating in accordance with examples of the invention.

FIG. 17 illustrates a diagrammatic representation of a machine in the exemplary form of a computer system 1700 within which a set of instructions, for causing the machine to perform any one or more of the methodologies discussed herein, may be executed. In alternative implementations, the machine may be connected (e.g., networked) to other machines in a LAN, an intranet, an extranet, or the Internet. The machine may operate in the capacity of a server or a client machine in client-server network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The exemplary computer system 1700 includes a processing device (processor) 1702, a main memory 1704 (e.g., read-only memory (ROM), flash memory, dynamic random access memory (DRAM) such as synchronous DRAM (SDRAM) or Rambus DRAM (RDRAM), etc.), a static memory 1706 (e.g., flash memory, static random access memory (SRAM), etc.), and a data storage device 1718, which communicate with each other via a bus 1708. Processor 1702 represents one or more general-purpose processing devices such as a microprocessor, central processing unit, or the like. More particularly, the processor 1702 may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processor 1702 may also be one or more special-purpose processing devices such as an application specific integrated circuit (ASIC), a field programmable gate array (FPGA), a digital signal processor (DSP), network processor, or the like. The processor 1702 is configured to execute instructions 1726 for performing the operations and steps discussed herein.

The computer system 1700 may further include a network interface device 11722. The computer system 1700 also may include a video display unit 1710 (e.g., a liquid crystal display (LCD), a cathode ray tube (CRT), or a touch screen), an alphanumeric input device 1712 (e.g., a keyboard), a cursor control device 1714 (e.g., a mouse), and a signal generation device 1720 (e.g., a speaker).

The data storage device 1718 may include a computer-readable storage medium 1724 on which is stored one or more sets of instructions 1726 (e.g., software) embodying any one or more of the methodologies or functions described herein. The instructions 1726 may also reside, completely or at least partially, within the main memory 1704 and/or within the processor 1702 during execution thereof by the computer system 1700, the main memory 1704 and the processor 1702 also constituting computer-readable storage media. The instructions 1726 may further be transmitted or received over a network 1774 via the network interface device 1722.

While the computer-readable storage medium 1724 is shown in an exemplary implementation to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium that is capable of storing, encoding or carrying a set of instructions for execution by the machine and that cause the machine to perform any one or more of the methodologies of the present disclosure. The term "computer-readable storage medium" shall accordingly be taken to include, but not be limited to, solid-state memories, optical media, and magnetic media.

In the foregoing description, numerous details are set forth. It will be apparent, however, to one of ordinary skill in the art having the benefit of this disclosure, that the present disclosure may be practiced without these specific details. In some instances, well-known structures and devices are shown in block diagram form, rather than in detail, in order to avoid obscuring the present disclosure.

Some portions of the detailed description have been presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like. It should be borne in mind, however, that all of these and similar terms are to be associated with the appropriate physical quantities and are merely convenient labels applied to these quantities.

Unless specifically stated otherwise as apparent from the following discussion, it is appreciated that throughout the description, discussions utilizing terms such as "segmenting", "analyzing", "determining", "enabling", "identifying," "modifying" or the like, refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices.

The disclosure also relates to an apparatus for performing the operations herein. This apparatus may be specially constructed for the required purposes, or it may include a general purpose computer selectively activated or reconfigured by a computer program stored in the computer. Such a computer program may be stored in a computer readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions.

The words "example" or "exemplary" are used herein to mean serving as an example, instance, or illustration. Any aspect or design described herein as "example' or "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form. Moreover, use of the term "an implementation" or "one implementation" or "an implementation" or "one implementation" throughout is not intended to mean the same implementation or implementation unless described as such.

Reference throughout this specification to "one implementation" or "an implementation" means that a particular feature, structure, or characteristic described in connection with the implementation is included in at least one implementation. Thus, the appearances of the phrase "in one implementation" or "in an implementation" in various places throughout this specification are not necessarily all referring to the same implementation. In addition, the term "or" is intended to mean an inclusive "or" rather than an exclusive "or."

It is to be understood that the above description is intended to be illustrative, and not restrictive. Many other implementations will be apparent to those of skill in the art upon reading and understanding the above description. The scope of the disclosure should, therefore, be determined with reference to the appended claims, along with the full scope of equivalents to which such claims are entitled.

The invention claimed is:

1. A method, comprising:
generating, by a radiation source, a beam of coherent radiation;
focusing, by traveling lens optics, the beam to generate multiple spots on a surface of a sample;
scanning the multiple spots together over the surface while varying at least one optical character of at least one spot of the multiple spots in alternation;
collecting, by collection optics, radiation scattered from the multiple spots and focusing the collected radiation to generate a pattern of interference fringes;
detecting, by a detection unit, changes in the pattern of interference fringes;
generating multiple images of non-continuous portions of the surface of the sample representative of near-field radiation in proximity to the surface of the sample, each image of the multiple images is associated with a certain value of the at least one optical character; and
classifying defects on the surface of the sample using the multiple images.

2. The method of claim 1, wherein the multiple spots comprise a first spot, a second spot, and a third spot, and wherein the traveling lens optics comprise an acousto-optic Bragg cell and an acoustic transducer coupled to the cell adapted to produce first, second, and third frequency-modulated acoustic pulses which travel along a length of the Bragg cell such that, when the beam of radiation passes through the Bragg cell, it is focused by the first, second, and third pulses so as to generate and scan the first, second, and third spots, respectively.

3. The method of claim 2, wherein the transducer is adapted to vary, in response to receiving a control signal from a controller, a relative timing and phase of the first, second, and third acoustic pulses to control a spacing and relative phase of the first, second and third spots.

4. The method of claim 3, wherein the second spot is formed between the first and third spots, and wherein the traveling lens optics are adapted to generate the first and third spots as being of a same phase and to generate the second spot as being phase shifted from the first and third spots.

5. The method of claim 3, wherein the traveling lens optics are adapted to control, in response to receiving the signal transmitted by the controller, at least one of a phase and amplitude of each one of the first, second and third spots to cause the pattern of interference fringes to remain substantially stationary at a certain optical plane regardless of topographic differences between different portions of the surface of the sample.

6. The method of claim 3, wherein the second spot is formed between the first and third spots, and wherein the traveling lens optics are adapted to vary, in response to receiving a signal transmitted by a controller, a phase differently between the second spot and a phase of the third and first spots while maintaining the second spot between the first and third spots.

7. The method of claim 1, wherein the collection optics comprise a beam stop which is arranged to block at least one interference fringe of the pattern of interference fringes from impinging on a detector of the detection unit.

8. The method of claim 1, wherein the traveling lens optics are further adapted to vary, in response to receiving a signal transmitted by a controller, a phase of the at least one spot in alternation between at least three different phase values to generate at least three images of the multiple images, each of the at least three images corresponds to a different phase value.

9. A system, comprising:
a radiation source adapted to generate a beam of coherent radiation;
traveling lens optics adapted to focus the beam to generate multiple spots on a surface of a sample and to scan the multiple spots together over the surface, the traveling lens optics being further adapted to, in response to receiving a signal from a controller, generate the multiple spots and to vary at least one optical character of at least one spot of the multiple spots in alternation;
collection optics comprising an objective lens and a beam splitter, the collection optics being positioned and adapted to collect the radiation scattered from the multiple spots and to focus the collected radiation to generate a pattern of interference fringes;
a detector adapted to detect changes in the pattern of interference fringes; and
processing hardware adapted to:
generate multiple images of non-continuous portions of the surface of the sample representative of near-field radiation in proximity to the surface of the sample, each image of the multiple images is associated with a certain value of the at least one optical character; and
classify defects on the surface of the sample using the multiple images.

10. The system of claim 9, wherein the multiple spots comprise a first spot, a second spot, and a third spot, and wherein the traveling lens optics comprise an acousto-optic Bragg cell and an acoustic transducer coupled to the cell adapted to produce first, second, and third frequency-modulated acoustic pulses which travel along a length of the Bragg cell such that, when the beam of radiation passes through the Bragg cell, it is focused by the first, second, and third pulses so as to generate and scan the first, second, and third spots, respectively.

11. The system of claim 10, wherein the transducer is adapted to vary a relative timing and phase of the first, second, and third acoustic pulses to control a spacing and relative phase of the first, second and third spots.

12. The system of claim 11, wherein the second spot is formed between the first and third spots, and wherein the traveling lens optics are adapted to generate the first and third spots as being of a same phase and to generate the second spot as being phase shifted from the first and third spots.

13. The system of claim 11, wherein the traveling lens optics are adapted to control at least one of a phase and amplitude of each one of the first, second and third spots to cause the pattern of interference fringes to remain substantially stationary at a certain optical plane regardless of topographic differences between different portions of the surface of the sample.

14. The system of claim 10, wherein the second spot is formed between the first and third spots, and wherein the traveling lens optics are adapted to vary a phase differently between the second spot and a phase of the third and first spots while maintaining the second spot between the first and third spots.

15. The system of claim 9, wherein the collection optics further comprise a beam stop which is arranged to block at least one interference fringe of the pattern of interference fringes from impinging on the detector.

16. The system of claim 9, wherein the traveling lens optics are further adapted to vary a phase of the at least one spot in alternation between at least three different phase values to generate at least three images of the multiple images, each of the at least three images corresponds to a different phase value.

\* \* \* \* \*